United States Patent [19]

Li

[11] 4,294,994
[45] Oct. 13, 1981

[54] PURIFICATION OF BISPHENOL-A

[75] Inventor: Ming K. Li, Schenectady, N.Y.

[73] Assignee: General Electric Company, Schenectady, N.Y.

[21] Appl. No.: 141,778

[22] Filed: Apr. 21, 1980

[51] Int. Cl.³ .............................................. C07C 37/70
[52] U.S. Cl. ...................................... 568/724; 568/749
[58] Field of Search ................................ 568/724, 749

[56] References Cited

U.S. PATENT DOCUMENTS 2,791,616  5/1957  Luten .................................... 568/720
3,111,544  11/1963  Joris ..................................... 568/724
3,936,507  2/1976  Ligorat et al. ....................... 568/724

Primary Examiner—Werren B. Lone
Attorney, Agent, or Firm—Joseph T. Cohen; James C. Davis, Jr.

[57] ABSTRACT

Pure bisphenol-A can be obtained by subjecting the adduct of the latter and phenol to spray drying conditions and recovering the bisphenol-A from the released phenol. The use of an inert liquid carrier for the adduct, such as acetone, facilitates the desired separation and purification of the bisphenol-A.

4 Claims, 1 Drawing Figure

U.S. Patent
Oct. 13, 1981
4,294,994
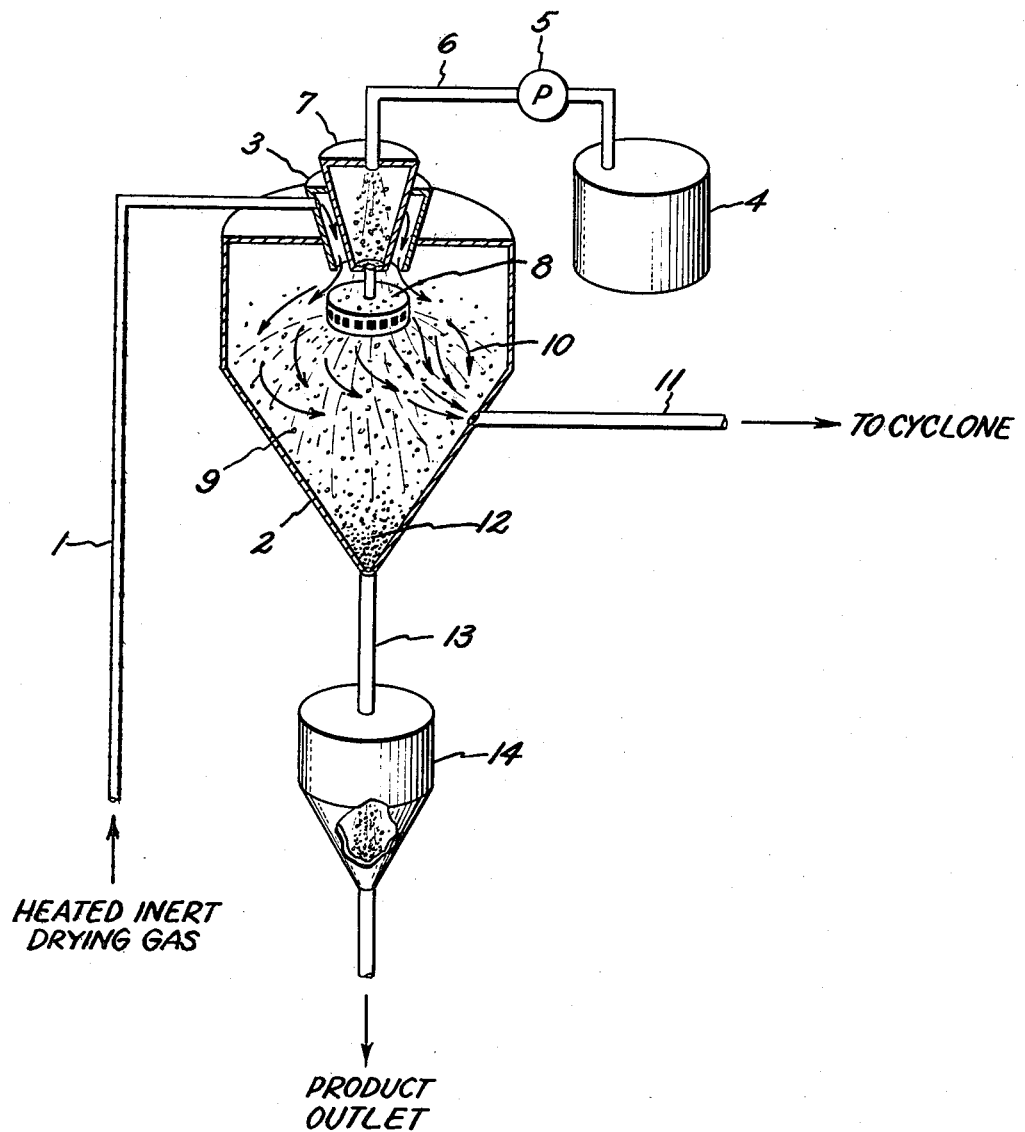

PURIFICATION OF BISPHENOL-A

This invention is concerned with the purification of 2,2-bis(4-hydroxyphenyl) propane (hereinafter identified as "bisphenol-A" or "BPA"). More particularly, the invention is directed to a method for recovering bisphenol-A in a purified state from a preformed adduct of the latter and phenol, and any excess phenol associated with the adduct, which method comprises subjecting the adduct of the aforesaid dihydroxydiphenyl propane and phenol to spray drying whereby the dihydroxydiphenyl propane is separated from the phenol and recovered in a highly purified state. The invention also includes the use of small amounts of a liquid carrier, specifically acetone, in at least 0.05%, by weight, carrier, based on the weight of the adduct up to a maximum of 20%, by weight, combined with the adduct, in order to facilitate separation and recovery of the highly purified bisphenol-A substantially free of phenol.

Bisphenol-A is commercially prepared by reacting phenol and acetone in the presence of an acidic material such as sulfuric acid, hydrochloric acid, cation exchange resins, etc. As a result of carrying out this reaction, the bisphenol-A produced is accompanied by undesirable impurities such as the 2-(4-hydroxyphenyl)-2-(2-hydroxyphenyl) propane (hereinafter identified as "o,p-isomer") having the formula

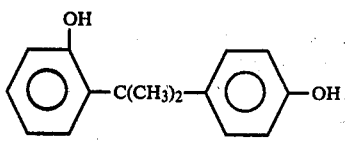

as well as other impurities including phenol itself used in making the bisphenol-A, a trishydroxyphenyl compound of the formula

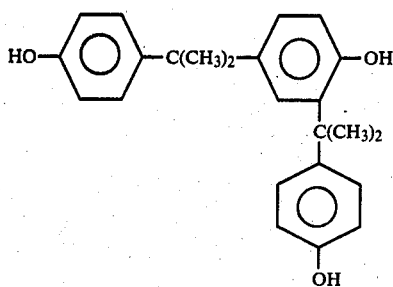

(hereinafter identified as "BPX-1", small amounts of other impurities such as the two compounds having the formulas

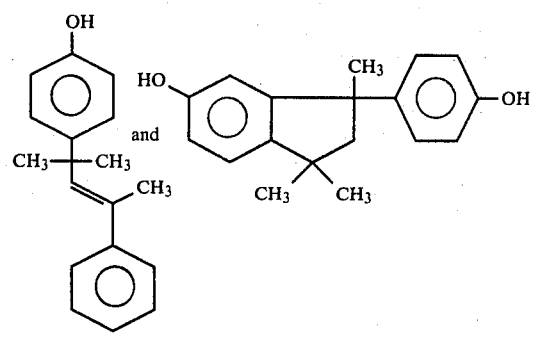

(hereinafter identified as "LD/CD", etc.

Since biphenol-A is used in making polycarbonate resins by reaction of the latter with either phosgene or diphenyl carbonate, or for making epoxy resins, both resins being used extensively in commercial applications involving molding, casting, and sheet forming purposes, it is highly important that the monomeric bisphenol-A used to make such resins be as pure as possible in order to avoid adverse effects on the properties of the polymers thus obtained.

The preparation of the bisphenol-A by the reaction of phenol and acetone is usually carried out in excess phenol (greater than 2 moles phenol per mole acetone). Upon sufficient cooling of the reaction product mixture, an adduct in which there is 1 mole of phenol per mole of bisphenol-A will crystallize out of the aforesaid product mixture. The isolated product, which is in a fairly pure state represents a starting point of making bisphenol-A of high purity.

One method for working with this adduct to arrive at a purified bisphenol-A is described in Luten U.S. Pat. No. 2,791,616 issued May 7, 1957. According to this patent, the adduct obtained as a result of carrying out the initial reaction in the presence of the acidic condensation catalyst, uses a large excess of water within a well-defined temperature range which serves to liberate the phenol from the adduct with the result that most of the phenol is dissolved in the water while substantially all the bisphenol-A remains behind in the solid state. However, this process suffers from several disadvantages. Excessive amounts of water are usually required. Also the water obtained containing the phenol, whether liberated from the adduct or the excess amount used in carrying out the initial condensation reaction, is in the form of a mixture which requires considerable processing and expenditure of energy in order to recover the phenol so that it can be used again for reaction with the acetone.

Another purification processing technique which has been employed after the adduct is broken into its components is to subject the bisphenol-A to high temperature distillation to separate the latter from the impurities. In the process of using the high temperatures required (even under vacuum conditions) some of the BPA is lost through degradation and tar formation, thus contributing to a process which does not permit optimum yields of the bisphenol-A in a highly purified state.

Unexpectedly, I have discovered that by a special treatment of the bisphenol-A-phenol adduct advantageously with a small amount of a liquid carrier having a boiling point below that of phenol and using a spray drying technique, the adduct is split so that highly purified bisphenol-A particles are obtained separately from the remainder of the adduct which consists mainly of phenol as well as the carrier fluid which may be used in the process, the bisphenol-A particles thus separated and isolated are of high purity and substantially colorless. The separated phenol and any acetone in combination thereof, can then be recycled with other amounts of phenol and acetone employed in requisite amounts in the presence of an acidic condensation catalyst to again form bisphenol-A which can be recycled by means of an adduct to this system which comprises the basis for my invention.

My newly discovered method has numerous advantages over the prior art methods for obtaining purified bisphenol-A. In the first place, it is essentially a single stage procedure. Moreover, since it falls into the general "non-solvent system" category, it satisfies many environmental obstacles which have been problems in the past. Additionally, in contrast to prior methods for obtaining high purity bisphenol-A, stringent conditions, such as high temperature, high vacuum, long residence time, and even multiple distillation stages and flaking operations are substantially avoided. Using the spray drying technique involved in the present invention, moderate temperatures at short residence times (usually less than 30 seconds) are employed, and consequently the bisphenol-A does not experience adverse heat history and is less susceptible to degradation and consequent increase in color. Finally, my invention comprises a one-stage spray drying system of a highly simplified character in an easily controllable process compared to those processes where multi-stages are used, such as crystallization, extraction, distillation, flaking operations, etc. This also enables one to realize capital cost advantages which compare favorably to prior efforts at purification of bisphenol-A.

After separation of the bisphenol-A, the phenol and acetone can easily be scrubbed and condensed with a suitable scrubbing agent and then be recycled back to a reactor without the need of further treatment, such as distillation or other separation procedures, to react again with required amounts of phenol and acetone to make bisphenol-A. In contrast to this, other organic-aqueous "solvent systems" previously employed require several subsequent steps to separate the solvents from the sizeable portions of the bisphenol-A and phenol residue to insure that the residue recycle stream is not contaminated with the solvent. Aqueous discharge streams also need further waste treatment, a step which is unnecessary in my invention.

A typical spray drying apparatus which can be employed in the practice of the present invention is found described in the attached single FIGURE, which represents a schematic drawing of a spray drying equipment suitable in my process.

In the accompanying drawing, a closed loop single stage spray dryer system is described having a rotary atomizer. In the drawing, an inlet tube 1 provides conduit for a heated inert drying gas, for instance, nitrogen, maintained at an elevated temperature (e.g., above 100° C., such as from 140° to 250° C.) which is introduced into the spray drying vessel 2 through a chamber 3. At the same time, a feed tank 4 is provided wherein the adduct in combination with the inert low boiling (below about 175° C.) carrier fluid advantageously is heated to a temperature of about 50° to 150° C., and this mixture in the molten state is pumped by means of a pumping apparatus 5 through a conduit 6 into a chamber 7 from where it passes into an atomizer wheel 8, which is turning at high speed (e.g., about 10,000 to 20,000 rpm) and which wheel has apertures at its periphery emitting the droplets derived from the molten adduct and liquid carrier through the orifices. After the molten adduct droplets emerge from the orifices, they come in contact with the heated inert gas which, in a matter of a few seconds (usually less than 30 seconds) causes evaporation of the phenol and any carrier fluid from the original molten adduct droplets to form a separate gaseous phase 10 comprising evaporated phenol, carrier fluid and inert gas. This gaseous phase is removed through conduit 11, while the particles of purified bisphenol-A 9 fall to the bottom of the spray dryer chamber 2 and are collected in a pourable mass 12. These particles of highly purified bisphenol-A then fall through a conduit 13 into a collecting chamber 14. The evaporated phase 10, can be reclaimed for its content of phenol, inert gas, and acetone. The mixture comprising the phenol and acetone can be combined with additional phenol and acetone in the presence of an acidic condensation catalyst to supply their requisite ingredient content to manufacture more bisphenol-A.

Alternatively, one can proceed with a modification of my invention by removing through conduit 11, all the evaporated products in drying chamber 2, including the separated bisphenol-A, phenol, acetone, and inert gas into a cyclone chamber, not shown, where solid bisphenol-A particles can be readily separated from the inert gas and the evaporated components, namely, the phenol and acetone.

The bisphenol-A product obtained from chamber 14 (or from the cyclone) can be used to make polycarbonate resins because it is in a highly purified state. Additionally, the purified bisphenol-A can be washed with methylene chloride as is more particularly disclosed and claimed in my U.S. Pat. No. 4,156,098 issued May 22, 1979 and assigned to the same assignee as the present invention.

The transformation of the fluid feed by means of spray drying into a dried, highly purified bisphenol-A product in one single operation is a unique feature of my invention. The ability of the bisphenol-A to be isolated rapidly from the molten adduct in the presence of the hot inert gas thereby avoids degradation or coloration of the bisphenol-A, something which often occurs when bisphenol-A is subjected to distillation to purify it.

The speed of the rotating atomizer wheel can be varied widely depending on the temperatures used for the inlet gas and the temperature at which the adduct is maintained. The adduct feed at times can either be pumped to the atomizer or fed by gravity so that contact between the heated inert gas and the emitted material from the atomizer wheel is readily facilitated.

In the practice of my invention, bisphenol-A-phenol adduct (which corresponds on a weight basis of about 70% bisphenol-A and 30% phenol), with small amounts of acetone, is introduced into the spray drying equipment, more particularly illustrated herein, whereby the mixture of the adduct and any impurities and acetone which may be present, are at a feed temperature within the range of 50°–150° C., preferably within the range of 55°–100° C. The inert gas, for example, nitrogen, which is used, can be introduced into the spray dryer at a temperature of about 150°–250° C. (or higher if desired) and preferably within the range of 175°–230° C. Under the above conditions, it will be found that the product outlet temperature, whether it be the purified bisphenol-A particles, or the remainder of the feedstock, namely the released phenol and acetone, is within the temperature range of 100°–150° C., and preferably within the range of 125°–145° C. Where scrubbing agents are used to cleanse the outlet products other than the bisphenol-A particles, one can employ for this purpose either acetone or mixtures of acetone and phenol. This scrubbing action can be carried out at rather low temperatures of the order of −15° to −20° C. and preferably from −10° to 10° C.

I have found that as little as 0.5% by weight, acetone based on the weight of the adduct, has an influential effect on the successful outcome of my process. The amount of acetone on a weight basis can range up to 20%, by weight, based on the weight of the adduct, although amounts in excess of 15%, by weight may not be necessary.

Although acetone is the preferred liquid carrier with the adduct, because the recovered acetone can be recycled with the recovered phenol to be mixed with additional amounts of phenol and acetone to make bisphenol-A, other liquid carriers having boiling points below phenol can be employed, where there is no intent to recycle the liquid carrier. Among such other liquid carriers may be mentioned, for instance, methanol, ethanol, toluene, methylene chloride, etc.

Although the bisphenol-A particles obtained as a result of practicing my above-described invention are in a highly purified state, it is possible that there will may be some residual impurities present, which although they may not be detrimental to polymers made with the bisphenol-A, still, anticipating room for improvement in properties of such polymers these crystals can be washed with either methylene chloride (as is described in my U.S. Pat. No. 4,156,098) or additional amounts of toluene, and thereafter dried to obtain a bisphenol-A which is exceptionally pure approaching 100% purity. When these highly purified bisphenol-A particles are used to make, for instance, polycarbonate resins, it will be found that the color properties of the polycarbonate resins are almost water-white thus pointing to possible expansion of uses of such resins in applications where color might be an important consideration.

My invention has major advantages over the process described in the above-mentioned Luten U.S. Pat. No. 2,791,616. Luten employs amounts of water for addition to the adduct which are quite large and which increase the complexity of the processing techniques and the isolation of the purified bisphenol-A. In my process, I do not employ any water which increases the cost and complexity of the procedure, and the time for carrying out the reaction takes place in a matter of seconds as contrasted to much longer times when using the Luten process.

The term "bisphenol-A-phenol adduct" as used herein is intended to mean either (1) the adduct which is obtained as a result of the reaction of the phenol and the acetone in the presence of an acidic condensation catalyst, as well as (2) a preformed adduct which is made from impure bisphenol-A which has been treated with a sufficient amount of phenol to form the adduct. The molar concentration of the adduct consists of 1 mole of the bisphenol-A and 1 mole of phenol, and, on a weight basis, represents approximately 70 percent of the bisphenol-A and 30 percent phenol.

In order that those skilled in the art may better understand how the present invention may be practiced, the following examples are given by way of illustration and not by way of limitation. Unless otherwise indicated, all parts of ingredients are by weight.

The bisphenol-A adduct used in the following tests can be prepared in various ways. One example of such preparation is as follows:

EXAMPLE 1

Crude bisphenol-A (obtained from the reaction of phenol and acetone in the presence of an acidic catalyst, such as $H_2SO_4$ is dissolved with stirring in a large excess of phenol at a temperature of about 95° C. The adduct which precipitates is isolated from the mother liquor consisting mostly of phenol and impurities. This procedure allows for a close simulation of the preparation of the preformed adduct that would be obtained in a bisphenol-A manufacturing plant.

EXAMPLE 2

Employing the illustrated spray drying equipment, the adduct which can be prepared as in Example 1, was introduced into the spray drying equipment under the conditions and with the results recited in Table 1. The inert carrier gas used was nitrogen gas, although any inert gas such as, helium, xenon, etc., can be used. All ingredients recited (acetone, bisphenol-A and phenol) are in parts, by weight, as found in the feed tank. The phenol and acetone recovered are essentially in the same amounts as introduced into the spray dryer.

TABLE 1

| Test No. | 1 | 2 | 3 | 4 |
|---|---|---|---|---|
| Acetone | 15 | 15 | 10 | 10 |
| Bisphenol-A | 55 | 55 | 59 | 59 |
| Phenol | 30 | 30 | 31 | 31 |
| Feed Temp. °C. | 70 | 60 | 85 | 100 |
| Inlet $N_2$ Gas Temp. °C. | 212 | 210 | 185 | 180 |
| Outlet Gas and Product Temp. °C. | 130 | 128 | 135–145 | 130 |
| Product Analysis (Purity) | | | | |
| Bisphenol-A | 99.03% | 99.62% | — | — |
| Phenol | 0.97% | 0.38% | — | — |
| *Cyclone Treatment | | | | |
| Bisphenol-A | — | — | 99.92% | 98.61% |
| Phenol | — | — | 0.08% | 1.39% |

*Derived from purification of entire product subjected to cyclone treatment and elimination of steps of removing bisphenol-A through conduit 13.

In carrying out the above tests, the bisphenol-A-phenol adduct combined with amounts of acetone recited in the table, was introduced into the spray dryer at varying feed temperatures while nitrogen gas was also being introduced at varying temperatures, all while the atomizer was revolving at a rate of about 10,000 to 20,000 rpm. The outlet gas temperature with the mixture of the phenol and acetone also varied depending on the conditions of introduction of the various ingredients and gas. Table 1 also shows the product (purity) analysis by means of percent of bisphenol-A and phenol found in the purified bisphenol-A particles. In tests 1 and 2, bisphenol-A particles were collected from chamber 14, while in tests 3 and 4, bisphenol-A particles were collected from the cyclone chamber referred to previously bypassing conduit 13 and collecting chamber 14.

It will of course be understood by those skilled in the art that in addition to the conditions and proportions of ingredients in the presence of the acetone which can be employed in the foregoing examples, other conditions and proportions of the mixture, filtering, purification, temperatures, ratios of the adduct to acetone, inert gases, etc., may be employed without departing from the scope of the claimed invention.

What I claim as new and desire to secure by Letters Patent of the United States is:

1. The method of recovering 2,2-bis(4-hydroxyphenyl) propane in a highly purified state which comprises subjecting a preformed isolated adduct of the aforesaid dihydroxydiphenyl propane and phenol containing at least 0.05%, by weight, of said adduct of acetone, to spray drying conditions at a temperature of from 50°–150° C. whereby the adduct is converted to the purified dihydroxydiphenyl propane and is recovered in a highly purified state and the acetone and phenol thereby produced are separately recovered.

2. The process as in claim 1 wherein an inert gas maintained at a temperature of at least 150° C. is introduced into the spray drying equipment so as to contact the molten adduct droplets derived from contacting the spray drying equipment whereby a separate gaseous phase is formed comprising the phenol from the adduct, the acetone, and the inert gas.

3. The process as in claim 2 wherein the inert gas is nitrogen.

4. The process as in claim 1 wherein the phenol and acetone recovered from the spray drying step are recycled to a reaction vessel containing requisite amounts of phenol acetone to form the aforesaid dihydroxydiphenyl propane in the presence of an acidic condensation catalyst.

* * * * *